United States Patent
Kobayashi et al.

[11] Patent Number: 5,229,238
[45] Date of Patent: Jul. 20, 1993

[54] ELECTROPHOTOGRAPHIC PHOTORECEPTOR COMPRISING A BENZODITHIAFULVENE DERIVATIVE CHARGE TRANSPORT MATERIAL

[75] Inventors: Tohru Kobayashi; Yoshimasa Matsushima; Toshimitsu Hagiwara, all of Tokyo, Japan

[73] Assignee: Takasago International Corporation, Tokyo, Japan

[21] Appl. No.: 691,883

[22] Filed: Apr. 26, 1991

[30] Foreign Application Priority Data

Apr. 27, 1990 [JP] Japan ................................. 2-110518
Mar. 8, 1991 [JP] Japan ................................. 3-125705

[51] Int. Cl.⁵ .......................... G03G 5/047; G03G 5/06
[52] U.S. Cl. ........................................ 430/58; 430/75; 430/79; 430/85; 430/59
[58] Field of Search .................. 430/83, 58, 75, 82, 430/59

[56] References Cited
FOREIGN PATENT DOCUMENTS 2396989 2/1979 France .

*Primary Examiner*—Marion E. McCamish
*Assistant Examiner*—Rosemary Ashton
*Attorney, Agent, or Firm*—Sughrue, Mion, Zinn, Macpeak & Seas

[57] ABSTRACT

An electrophotographic photoreceptor is disclosed, comprising an electroconductive support having a light-sensitive layer containing a charge generating substance and a charge transporting substance, wherein said charge transporting substance is a 1,4-benzodithiafulvene derivative represented by formula (I):

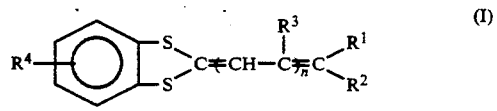

wherein $R^1$ represents a lower alkyl group, a benzyl group, a naphthyl group, or a phenyl group which may contain a substituent; $R^2$ represents a phenyl group which may contain a substituent or an N-alkyl-substituted carbazole group; $R^3$ represents a hydrogen atom or a phenyl group which may contain a substituent; $R^4$ represents a hydrogen atom, a lower alkyl group, a hydroxyl group, or an alkoxy group or an aryloxy group represented by $OR^5$; $R^5$ represents a lower alkyl group, a benzyl group, or a phenyl group which may contain a substituent; and n represents an integer of 0 or 1.

3 Claims, 3 Drawing Sheets

ELECTROPHOTOGRAPHIC PHOTORECEPTOR COMPRISING A BENZODITHIAFULVENE DERIVATIVE CHARGE TRANSPORT MATERIAL

FIELD OF THE INVENTION

The present invention relates to an electrophotographic photoreceptor. More particularly, the present invention relates to an electrophotographic photoreceptor comprising an electroconductive support having thereon a light-sensitive layer containing a charge generating substance and a specific charge transporting substance.

BACKGROUND OF THE INVENTION

In recent years, as electrophotographic photoreceptor materials there have been widely known inorganic photoconductive substances such as α-selenium, cadmium sulfide and α-silicon and organic photoconductive substances such as poly-N-vinylcarbazole and polyvinyl anthracene. However, these photoconductive substances have not a few disadvantages in price, properties and toxicity.

A mode has been often proposed which comprises allowing two functions of such photoconductive substances, i.e., generation of charges and transportation of charges thus generated to be performed by separate organic compounds in order to eliminate these disadvantages and provide a higher sensitivity. In this mode, it is expected that the lamination of a substance which exhibits a high charge carrier generation efficiency (charge generating substance) and a substance which exhibits a high capability of transporting charges (charge transporting substance) can provide a high-sensitivity electrophotographic photoreceptor. However, it is not always possible to simultaneously attain those various properties required for the electrophotographic photoreceptor, that is, high surface potential, high charge retention ability, high light sensitivity and little residual potential.

Thus, as charge transporting substances there have been recently proposed heterocyclic, arylamine, hydrazone and thioether compounds. As thioether compounds there have been proposed styrylthioether and 4-arylbutadienylthioether derivatives as disclosed in JP-A-1-140162 (the term "JP-A" as used herein means an "unexamined published Japanese patent application") and styrylphenylthioether derivatives as disclosed in JP-A-62-134652.

However, any of electrophotographic photoreceptors comprising these thioether compounds as a charge transporting substance leaves to be desired in light sensitivity. The compounds as disclosed in JP-A-1-140162 are disadvantageous in that they can be difficultly dissolved in a binder polymer during the formation of a light-sensitive layer.

Thus, various electrophotographic photoreceptors comprising a function-separating type light-sensitive layer comprising a combination of a charge generating substance and a charge transporting substance have been proposed. However, any of these electrophotographic photoreceptors leaves to be desired in light sensitivity. Furthermore, these electrophotographic photoreceptors have practical disadvantages that when used repeatedly in accordance with an electrophotographic process, they are subject to reduction in the capability of recovering the original chargeability (light fatigue), rise in the residual potential or reduction in the life thereof. As electrophotographic mode copying machines and printers have recently showed a progress in printing speed and miniaturization, electrophotographic photoreceptors have been desired to exhibit a high-speed responce. However, no electrophotographic photoreceptors have satisfied these requirements.

SUMMARY OF THE INVENTION

It is therefore an object of the present invention to provide an electrophotographic photoreceptor which exhibits a sufficiently high sensitivity, low residual potential and little light fatigue.

Paying an attention to thioether derivatives as charge transporting substances, the inventors have made extensive studies in quest of compounds suitable for the preparation of an electrophotographic photoreceptor which exhibits high performance. As a result, it has now been found that specific 1,4-benzodithiafulvene derivatives exhibit excellent electrophotographic properties, i.e., high sensitivity, low residual potential, and little light fatigue even after repeated use, leading to accomplishment of the present invention.

This object of the present invention can be accomplished with an electrophotographic photoreceptor comprising an electroconductive support having thereon a light-sensitive layer containing a charge generating substance and a charge transporting substance, wherein said charge transporting substance is a 1,4-benzodithiafulvene derivative represented by formula (I):

wherein $R^1$ represents a lower alkyl group, a benzyl group, a naphthyl group, or a phenyl group which may contain a substituent; $R^2$ represents a phenyl group which may contain a substituent or an N-alkyl-substituted carbazole group; $R^3$ represents a hydrogen atom or a phenyl group which may contain a substituent; $R^4$ represents a hydrogen atom, a lower alkyl group, a hydroxyl group, or an alkoxy group or an aryloxy group represented by $OR^5$; $R^5$ represents a lower alkyl group, a benzyl group, or a phenyl group which may contain a substituent; and n represents an integer of 0 or 1.

DETAILED DESCRIPTION OF THE INVENTION

Examples of the lower alkyl group represented by $R^1$ in formula (I) include straight and branched chain alkyl groups having from 1 to 4 carbon atoms.

Examples of the phenyl group which may contain a substituent, represented by $R^1$, $R^2$ or $R^3$, include a phenyl group; an alkoxyphenyl group; a methylenedioxyphenyl group; a lower alkyl-substituted phenyl group such as a tolyl group; a halogen-substituted phenyl group; and an N,N-di-substituted aminophenyl group such as an N,N-dialkylaminophenyl group and an N,N-diarylaminophenyl group. The position at which the substituent is connected to the phenyl group may be any of the ortho-position, meta-position and para-position, most preferably the para-position in view of ease of synthesis. Two or three of $R^1$, $R^2$ and $R^3$ may be the same. If $R^1$ is a naphthyl group, the α-position or β-position of the naphthyl group may be connected to the olefinic carbon. If $R^2$ is an N-alkyl-substituted carbazole group, the 3-position of the carbazole group is preferably connected to the olefinic carbon.

Examples of the lower alkyl group represented by $R^4$ include straight and branched chain alkyl groups having from 1 to 4 carbon atoms. Examples of the alkoxy group or aryloxy group $OR^5$ represented by $R^4$ include a methoxy group, an ethoxy group, a benzyloxy group, and a phenoxy group.

Specific examples of the 1,4-benzodithiafulvene derivative represented by formula (I) of the present invention include the following Illustrative Compounds (1) to (52), but the present invention should not be construed as being limited thereto.

(1)

(2)

(3)

(4)

(5)

(6)

(7)

(8)

(9)

(10)

-continued

(11)

(12)

(13)

(14)

(15)

(16)

(17)

(18)

(19)

(20)

(21)

(22)

(23)

(24)

(25)

(26)

(27)

(28)

-continued (29)

(30)

(31)

(32)

(33)

-continued

(34)

(35)

(36)

(37)

(38)

(39)

(40)

(41)

(42)

(43)

(44)

(45)

(46)

(47)

(48)

(49)

(50)

(51)

(52)

Preparation of Compound (I)

The synthesis of these compounds can be accomplished by the following reaction scheme in accordance with the Wittig-Horner reaction [K. AKIBA et al., Synthesis, p. 861 (1977)].

wherein $R^1$, $R^2$, $R^3$, $R^4$ and n are as defined above; and $R^6$ represents a methyl group or an ethyl group.

Specifically, the desired 1,4-benzodithiafulven derivative (I) can be obtained by subtracting the active proton from a 2-(O,O-dialkylphosphonyl)-1,3-benzodithiol derivative (III) with a base such as n-butyl lithium, potassium t-butoxide, sodium methoxide and sodium amide to form an anion, and then allowing the anion to react with a carbonyl compound (II).

The synthesis of the 2-(O,O-dialkylphosphonyl)-1,3-benzodithiol derivative (III) as a starting material can be accomplished by the following reaction scheme in accordance with e.g., the method proposed by NAKAYAMA et al. [Yuki Gosei Kagaku (Organic Synthetic Chemistry), 37 (8) p. 655 (1979)].

-continued wherein $R^4$ and $R^6$ are as defined above.

Specifically, the desired compound (III) can be obtained by converting an anthranilic acid derivative (IV) to a 2-isopentyloxy-1,3-benzodithiol derivative (V) with isoamyl nitrile, isoamyl alcohol and carbon disulfide, converting the derivative (V) to a 1,3-benzodithiolium tetrafluoroborate derivative (VI) with hydrofluoroboric acid and then allowing the derivative (VI) to react with a trialkyl phosphonate.

The synthesis of the carbonyl compound represented by formula (II) can be accomplished by the following reaction scheme.

wherein $R^1$, $R^2$ and $R^3$ are as defined above; Compound (II-a) is a compound wherein n is 0 in formula (II); and Compound (II-b) is a compound wherein n is 1 in the general formula (II).

Specifically, the ketone derivative (II-a) wherein n is 0 in formula (II) can be obtained by allowing a nitrile compound represented by formula (VII) to react with a Grignard reagent (VIII), followed by hydrolysis under acidic conditions. Furthermore, the acrolein derivative (II-b) wherein n is 1 in formula (II) can be easily obtained by allowing the ketone derivative (II-a) to react with a Grignard reagent represented by formula (IX) to obtain an alcohol compound, dehydrating the alcohol compound with an acidic catalyst to obtain an olefin compound (X) and then allowing the olefin compound (X) to react with a Vilsmeier reagent prepared from dimethylformamide (DMF) and phosphorus oxychloride in accordance with the method proposed by H. Lorenz et al. [*Helv. Chim. Acta*, 28, pp. 600-612 (1945)].

Electrophotographic Photoreceptor

The electrophotographic photoreceptor of the present invention will be described with reference to a typical example thereof.

Figure 1:
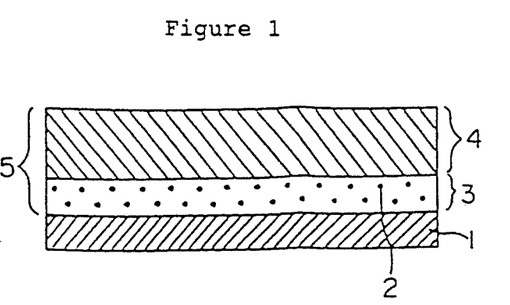
FIGS. 1, 2 and 3 show each a cross-sectional view illustrating an example of the electrophotographic photoreceptor of the present invention.

FIG. 1 illustrates an example of the electrophotographic photoreceptor of the present invention, which comprises an electroconductive support 1 having thereon a light-sensitive layer 5 comprising a charge generating layer 3 mainly containing a charge generating substance 2 and a charge transporting layer 4 uniformly containing a compound represented by formula (I) of the present invention.

In the photoreceptor shown in FIG. 1, a light which has been transmitted by the charge transporting layer reaches the charge generating substance 2 dispersed in the charge generating layer to generate charges which are then injected into the charge transporting layer 4 to thereby transport the charges.

In order to prepare the photoreceptor shown in FIG. 1, a charge generating layer is formed on an electroconductive support by any suitable method such as (1) vacuum deposition of a charge generating substance, (2) coating a dispersion obtained by dispersing finely divided grains of a charge generating substance and optionally, a binder, followed by drying and (3) coating a solution of a charge generating substance in a proper solvent, followed by drying. On the charge generating layer thus formed is then coated a solution containing a compound represented by formula (I) as a charge transporting substance and a binder to form a charge transporting layer. There is thus obtained a photoreceptor. The coating of the solution can be accomplished by usual means of, e.g., a doctor blade or a wire bar.

The thickness of the charge generating layer is normally in the range of 5 μm or less, and preferably 2 μm or less. The thickness of the charge transporting layer is normally in the range of from 3 to 50 μm, and preferably from 5 to 20 μm. The proportion of the compound represented by formula (I) to be incorporated in the charge transporting layer is normally in the range of from 10 to 90% by weight (hereinafter merely %), and preferably from 30 to 70%. The compound represented by formula (I) may be mixed with other charge generating substances to form a charge transporting layer.

As the electroconductive support there can be used plates, foils or pipes of metals such as aluminum, aluminum-deposited plastic film or paper which has been rendered electrically conductive.

As the binder there can be used polyester resins, polyvinyl chloride resins, acrylic resins, methacrylic resins, polystyrene resins, polycarbonate resins or the like. Particularly preferred among these resins are polyester resins and polycarbonate resins.

The charge generating substance of the present invention generally absorbs a light to generate charges. Examples of such a substance include inorganic materials such as amorphous selenium, arsenic selenide, cadmium sulfide and amorphous silicon; and organic materials such as azo pigments, phthalocyanine pigments, indigo pigments, perylene pigments, squarylium pigments, polycyclic quinone pigments, pyrylium dyes and pyrrolopyrrole pigments.

Figure 2:
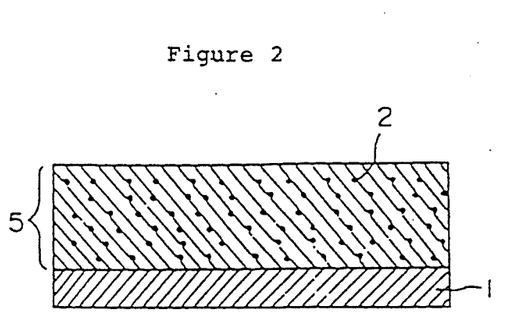
Figure 3:
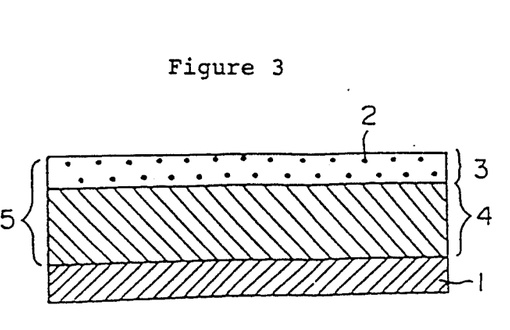

FIGS. 2 and 3 illustrate other examples of the electrophotographic photoreceptor of the present invention. In FIG. 2, the electrophotographic photoreceptor comprises an electroconductive support 1 having thereon a light-sensitive layer 5 formed by coating thereon a coating solution containing a charge transporting substance including a compound represented by formula (I) uniformly dissolved in a dispersion obtained by dispersing finely divided grains of a charge generating substance together with a binder, followed by drying. The thickness of the light-sensitive layer 5 is normally in the range of from 5 to 50 μm, and preferably from 10 to 25 μm.

In FIG. 3, the electrophotographic photoreceptor comprises an electroconductive support 1 having thereon a light-sensitive layer 5 formed by coating thereon a charge transporting substance including a compound represented by formula (I) to form a charge transporting layer 4 and further coating thereon a charge generating substance 2 to form a charge generating layer 3, as opposed to the structure shown in FIG. 1. A subbing layer may be optionally provided between the electroconductive support 1 and the light-sensitive layer 5. As the material for such a subbing layer there may be used polyamides, polyurethanes, polyvinyl alcohol, casein, nitrocellulose, gelatin or the like. The thickness of such a subbing layer is preferably in the range of from 0.1 to 1 μm.

The present invention will be further described in the following Synthesis Examples, Examples and Comparative Examples, but the present invention should not be construed as being limited thereto.

The measurements of the physical properties in the Synthesis Examples were conducted by means of the following measuring equipment.

$^1$H-NMR spectrum: Type AM-400 apparatus (400 MHz; available from Bruker Inc.); Internal standard: tetramethylsilane MS spectrum: Type M80B apparatus (available from Hitachi, Ltd.)

SYNTHESIS EXAMPLE 1

Synthesis of 2-isopentyloxy-1,3-benzodithiol (V)

42.1 g (0.36 mole) of isoamyl nitrile, 52.8 g (0.60 mole) of isoamyl alcohol and 150 ml of carbon disulfide were dissolved in 800 ml of 1,2-dichloroethane. The reaction solution was mildly heated under reflux at a temperature of about 80° C. A solution of 41.1 g (0.30 mole) of anthranilic acid in 100 ml of dioxane was added dropwise to the reaction solution over 1.5 hours. The reaction solution was further heated under reflux for an additional 30 minutes. The resulting mixture was washed successively with water, a saturated aqueous solution of sodium carbonate and water, and then dried over magnesium sulfate. The resulting organic solution was concentrated under reduced pressure. The residue was then purified through silica gel column chromatography (75 to 230 mesh; eluent: benzene) to obtain 28.8 g (yield: 40%) of the desired compound (V) as a pale yellow oil. The physical properties of the compound were as follows:

Boiling point: 122°–124° C./0.1 mmHg $^1$H-NMR (CDCl$_3$) δ ppm: 0.84 (d, J=7.0 Hz, 6H), 1.35–1.50 (m, 2H), 1.55–1.80 (m, 1H), 3.45 (t, J=7.0 Hz, 2H), 6.78 (s, 1H), 7.10 (AA'BB' system, 2H), 7.35 (AA'BB' system, 2H)

MS (m/e value): 241 (M+), 170, 153, 143, 109, 78, 32

SYNTHESIS EXAMPLE 2

Synthesis of 1,3-benzodithiolium tetrafluoroborate (VI)

16.0 g (0.067 mole) of 2-isopentyloxy-1,3-benzodithiol (V) obtained in Synthesis Example 1 was dissolved in 200 ml of acetic anhydride. A 42% aqueous solution of hydrofluoroboric acid was added dropwise to the reaction solution in 30 minutes under cooling with ice. After the reaction solution was stirred at room temperature for 30 minutes, 200 ml of diethyl ether was added thereto. The formed salt was filtered off and washed with 100 ml of diethyl ether. The resulting salt was dried to obtain 12.0 g (yield: 50%) of the desired compound (VI) as a white crystal (decomposition temperature: 150°–151° C.). The physical properties of the compound were as follows:

$^1$H-NMR (CF$_3$CO$_2$D) δ ppm: 8.20–8.25 (AA'BB' system, 2H) 8.75–8.82 (AA'BB' system, 2H), 11.5 (s, 1H)

SYNTHESIS EXAMPLE 3

Synthesis of 2-(O,O-dimethylphosphonyl)-1,3-benzodithiol (III)

12.0 g (0.05 mole) of 1,3-benzodithiolium tetrafluoroborate (VI) obtained in Synthesis Example 2 and 7.9 g (0.05 mole) of sodium iodide were dissolved in 200 ml of acetonitrile with stirring. 6.5 g (0.05 mole) of trimethyl phosphonate was gradually added dropwise to the reaction solution under cooling with ice. The reaction mixture was then stirred at room temperature overnight. The resulting mixture was concentrated under reduced pressure. The residue was stirred together with 150 ml of water and extracted with 150 ml of benzene. The benzene phase was dried over magnesium sulfate and concentrated to obtain 12.5 g of the desired compound in the form of crude crystal. The crude crystal was recrystallized from a mixture of 200 ml of hexane and 50 ml of ethyl acetate to obtain 10.2 g (yield: 78%) of the desired compound (III) as a white crystal (m.p. 121°–122° C.). The physical properties of the compound were as follows:

$^1$H-NMR (CDCl$_3$) δ ppm: 3.76 (s, 3H), 3.81 (s, 3H), 4.90 (d, J=5.0 Hz, 1H), 7.05 (AA'BB' system, 2H), 7.18 (AA'BB' system, 2H)

MS (m/e value): 262 (M+), 153, 121, 109, 77

SYNTHESIS EXAMPLE 4

Synthesis of Illustrative Compound (1)

4.0 ml (6.40 mmole) of a 1.6 M hexane solution of n-butyl lithium was gradually added to a solution of 1.7 g (6.48 mmole) of 2-(O,O-dimethylphosphonyl)-1,3-benzodithiol (III) prepared in Synthesis Example 3 in 70 ml of tetrahydrofuran at a temperature of −65° to −60° C. The reaction solution was then stirred at the same temperature for 10 minutes. A solution of 1.7 g (5.9 mmole) of 4-N,N-diphenylaminoacetophenone in 20 ml of tetrahydrofuran was grandually added to the reaction solution at the same temperature. The reaction temperature was then allowed to rise to room temperature overnight. The reaction mixture was poured into 100 ml of a saturated aqueous ammonium chloride solution. The mixture was then extracted with 100 ml of diethyl ether twice. The extract was dried over magnesium sulfate and concentrated. The residue was purified through silica gel column chromatography (70 to 230 mesh; 2 cm dia.×50 cm length; eluent: benzene) to obtain 2.5 g of an oily matter. The oily matter was then crystallized from a mixture of 20 ml of hexane and 5 ml of diethyl ether to obtain 1.74 g (yield: 70%) of Illustrative Compound (1) (m.p. 128°–130° C.) as a crystal. The physical properties of the compound were as follows:

$^1$H-NMR ($C_6D_6$) δ ppm: 1.60 (s, 3H), 6.20–6.28 (m, 2H), 6.30–6.38 (m, 1H), 6.41–6.50 (m, 3H), 6.58–6.72 (m, 10H), 6.72–6.82 (m, 2H)

MS (m/e value): 423 (M+), 270, 211, 167, 153

SYNTHESIS EXAMPLE 5

Synthesis of Illustrative Compound (6)

2.1 g (8.00 mmole) of 2-(O,O-dimethylphosphonyl)-1,3-benzodithiol, 5.7 ml (9.12 mmole) of a 1.6 M hexane solution of n-butyl lithium and 2.0 g (7.89 mmole) of 4-N,N-diethylaminobenzophenone were treated in the same manner as in Synthesis Example 4 to obtain 1.01 g (yield: 33%) of Illustrative Compound (6) (m.p. 119°–121° C.) as a crystal. The physical properties of the compound were as follows:

$^1$H-NMR ($C_6D_6$) δ ppm: 0.89 (t, J=7.0 Hz, 6H), 2.95 (q, J=7.0 Hz, 4H), 6.50–6.57 (AA'XX' system, 2H), 6.60–6.67 (m, 2H), 6.70–6.80 (m, 2H), 7.08 (t, J=8.0 Hz, 1H), 7.20 (t, J=8.0 Hz, 2H), 7.35–7.42 (AA'XX' system, 2H), 7.55 (d, J=8.2 Hz, 2H)

MS (m/e value) 389 (M+), 374, 345

SYNTHESIS EXAMPLE 6

Synthesis of Illustrative Compound (7)

1.6 g (6.10 mmole) of 2-(O,O-dimethylphosphonyl)-1,3-benzodithiol, 3.9 ml (6.24 mmole) of a 1.6 M hexane solution of n-butyl lithium and 2.0 g (5.72 mmole) of 4-N,N-diphenylaminobenzophenone were treated in the same manner as in Synthesis Example 4 to obtain 2.3 g (yield: 83%) of Illustrative Compound (7) (m.p. 136°–137° C.) as a crystal. The physical properties of the compound were as follows:

$^1$H-NMR ($C_6D_6$) δ ppm: 6.58–6.65 (m, 2H), 6.65–6.79 (m, 2H), 6.80–6.87 (m, 2H), 6.95–7.10 (m, 11H), 7.10–7.23 (m, 2H), 7.25–7.30 (AA'XX' system, 2H), 7.38–7.44 (m, 2H), MS (m/e value): 458 (M+), 165

SYNTHESIS EXAMPLE 7

Synthesis of Illustrative Compound (11)

2.1 g (8.0 mmole) of 2-(O,O-dimethylphosphonyl)-1,3-benzodithiol, 6.0 ml (9.6 mmole) of a 1.6 M hexane solution of n-butyl lithium and 1.7 g (7.0 mmole) of 4,4'-dimethoxybenzophenone were treated in the same manner as in Synthesis Example 4 to obtain 1.4 g (yield: 53%) of Illustrative Compound (11) (m.p. 98°–99° C.) as a crystal. The physical properties of the compound were as follows:

$^1$H-NMR ($C_6D_6$) δ ppm: 3.30 (s, 6H), 6.60–6.68 (AA'BB' system, 2H), 6.75–6.82 (AA'BB' system, 2H), 6.78–6.83 (AA'XX' system, 4H), 7.35–7.40 (AA'XX' system, 4H)

MS (m/e value): 377 (M+), 259, 211, 183

SYNTHESIS EXAMPLE 8

Synthesis of Illustrative Compound (15)

2.0 g (7.63 mmole) of 2-(O,O-dimethylphosphonyl)-1,3-benzodithiol, 4.8 ml (7.68 mmole) of a 1.6 M hexane solution of n-butyl lithium and 3.2 g (7.62 mmole) of 4-N,N-diethylamino-4'-N,N-diphenylaminobenzophenone were treated in the same manner as in Synthesis Example 4 to obtain 1.8 g (yield: 42%) of Illustrative Compound (15) (m.p. 175°–177° C.) as a crystal. The physical properties of the compound were as follows:

$^1$H-NMR ($C_6D_6$) δ ppm: 0.88 (t, J=7.0 Hz, 6H), 2.95 (q, J=7.0 Hz, 4H), 6.52–6.60 (AA'XX' system, 2H), 6.60–6.68 (m, 2H), 6.75–6.88 (m, 4H), 6.97–7.05 (m, 4H), 7.05–7.13 (m, 6H), 7.40–7.48 (m, 4H)

MS (m/e value): 556 (M+), 528, 512

SYNTHESIS EXAMPLE 9

Synthesis of Illustrative Compound (16)

2.0 g (7.63 mmole) of 2-(O,O-dimethylphosphonyl)-1,3-benzodithiol, 4.8 ml (7.68 mmole) of a 1.6 M hexane solution of n-butyl lithium and 3.6 g (7.16 mmole) of 4,4'-bis-N,N-diphenylaminobenzophenone were treated in the same manner as in Synthesis Example 4 to obtain 2.1 g (yield: 45%) of Illustrative Compound (16) (m.p. 185°–187° C.) as a crystal. The physical properties of the compound were as follows:

$^1$H-NMR ($C_6D_6$) δ ppm: 6.60–6.80 (AA'BB' system, 4H), 6.80–6.89 (m, 4H), 6.95–7.13 (m, 20H), 7.28–7.38 (AA'XX' system, 4H)

MS (m/e value): 655, 654, 653, 651 (M+), 326

SYNTHESIS EXAMPLE 10

Syntheis of Illustrative Compound (19)

2.1 g (8.00 mmole) of 2-(O,O-dimethylphosphonyl)-1,3-benzodithiol, 5.5 ml (8.8 mmole) of a 1.6 M hexane solution of n-butyl lithium and 2.1 g (7.02 mmole) of 3-(N-ethyl)-carbazoylphenyl ketone were treated in the same manner as in Synthesis Example 4 to obtain 2.3 g (yield: 75%) of Illustrative Compound (19) (m.p. 94°–97° C.) as a crystal. The physical properties of the compound were as follows:

$^1$H-NMR ($C_6D_6$) δ ppm: 0.90, 0.92 (t, J=7.3 Hz, 3H), 3.68, 3.90 (q, J=7.2 Hz, 2H), 6.58–6.68 (m, 2H), 6.68–6.76 (m, 1H), 6.76–6.85 (m, 1H), 7.00–7.10 (m, 3H), 7.10–7.28 (m, 3H), 7.38 (t, J=8.5 Hz, 1H), 7.50 (d, J=8.4 Hz, 1H), 7.60 (d, J=8.4 Hz, 2H), 7.95 (d, J=8.5 Hz, 1H), 8.30 (s, 1H)

MS (m/e value): 435 (M+), 420, 406, 280, 268

SYNTHEIS EXAMPLE 11

Synthesis of Illustrative Compounds (25) and (26)

2.2 g (7.97 mmole) of 2-(O,O-dimethylphosphonyl)-5-methyl-1,3-benzodithiol, 4.8 ml (7.68 mmole) of a 1.6 M hexane solution of n-butyl lithium and 3.2 g (7.62 mmole) of 4-N,N-diethylamino-4'-N,N-diphenylaminobenzophenone were treated in the same manner as in Synthesis Example 4 to obtain 1.7 g (yield: 39%) of a mixture of Illustrative Compounds (25) and (26) (m.p. 181°–182 ° C.) in the form of crystal. The physical properties of the mixture were as follows:

$^1$H-NMR ($C_6D_6$) δ ppm: 0.89 (t, J=7.0 Hz, 6H), 1.87 (d, J=5.7 Hz, 3H), 2.98 (q, J=7.0 Hz, 4H), 6.49 (d, J=7.6 Hz, 1H), 6.57 (d, J=8.9 Hz, 2H), 6.60 (s, 1H), 6.75 (t, J=8.3 Hz, 1H), 6.86 (t, J=7.3 Hz, 2H), 7.05 (t, J=7.6 Hz, 4H), 7.07–7.13 (m, 6H), 7.42–7.49 (m, 4 H), MS (m/e value): 570 (M+), 541, 526

SYNTHESIS EXAMPLE 12

Synthesis of Illustrative Compound (27)

2.0 g (7.25 mmole) of 2-(O,O-dimethylphosphonyl)-5-methyl-1,3-benzodithiol, 4.5 ml (7.2 mmole) of a 1.6 M hexane solution of n-butyl lithium and 3.0 g (6.97 mmole) of 4,4'-bis-N,N-diphenylaminobenzophenone were treated in the same manner as in Synthesis Example 4 to obtain 3.0 g (yield: 75%) of Illustrative Compound (27) (m.p. 165°–167° C.) as a crystal. The physical properties of the compound were as follows:

$^1$H-NMR (C$_6$D$_6$) δ ppm: 1.87 (s, 3H), 6.48 (d, J=8.0 Hz, 1H), 6.59 (s, 1H), 6.70 (d, J=8.0 Hz, 1H), 6.81–6.87 (m, 4H), 7.00–7.12 (m, 20H), 7.30–7.38 (m, 4H)

MS (m/e value): 666 (M+), 333

SYNTHESIS EXAMPLE 13

Synthesis of Illustrative Compound (34)

2 g (7.62 mmole) of 2-(O,O-dimethylphosphonyl)-1,3-benzodithiol and 2.5 g (6.7 mmole) of 3-(p-diphenylaminophenyl)-3-phenylacrolein were dissolved in 50 ml of dried N,N-dimethylformamide. 900 mg (8.02 mmole) of potassium t-butoxide was added to the solution at room temperature in 30 minutes. The reaction solution was stirred to undergo reaction at room temperature for 5 hours. The reaction solution was poured into 100 ml of water and extracted with 150 ml of a mixture of benzene and diethyl ether (1:1 by volume) twice. The extract was dried over magnesium sulfate and concentrated. The residue was purified through silica gel column chromatography (70 to 230 mesh; 2 cm dia.×50 cm length; eluent: benzene) to obtain 3.7 g of an oily matter. The oily matter was crystallized from a mixture of 20 ml of ethanol and 5 ml of ethyl acetate to obtain 2.02 g (yield: 59%) of Illustrative Compound (34) (m.p. 175°–178° C.) as a crystal. The physical properties of the compound were as follows:

$^1$H-NMR (C$_6$D$_6$) δ ppm: 6.42 (d, J=11.3 Hz, 1H), 6.56–6.67 (m, 3H), 6.75–6.78 (m, 1H), 6.81–6.89 (m, 3H), 6.93–6.99 (AA'XX' system, 2H), 7.00–7.15 (m, 11H), 7.18–7.23 (AA'XX' system, 2H), 7.23–7.27 (m, 2H)

MS (m/e value): 511 (M+), 371, 310, 268, 258, 191, 158

SYNTHESIS EXAMPLE 14

Synthesis of Illustrative Compound (35)

3.0 g (11.4 mmole) of 2-(O,O-dimethylphosphonyl)-1,3-benzodithiol, 3.0 g (11.2 mmole) of 3,3-bis(p-dimethoxyphenyl)-acrolein and 1.3 g (11.6 mmole) of potassium t-butoxide were treated in the same manner as in Synthesis Example 13 to obtain 2.1 g (yield: 46%) of Illustrative Compound (35) (m.p. 107°–109° C.) as a crystal. The physical properties of the compound were as follows:

$^1$H-NMR (C$_6$D$_6$) δ ppm: 3.30, 3.35 (s, 6H), 6.55 (d, J=11.2 Hz, 1H), 6.58–6.68 (m, 3H), 6.70–6.83 (m, 6H), 7.18–7.38 (AA'XX' system, 4H), MS (m/e value): 404 (M+), 389, 264, 153

SYNTHESIS EXAMPLE 15

Synthesis of Illustrative Compound (38)

2.5 g (9.53 mmole) of 2-(O,O-dimethylphosphonyl)-1,3-benzodithiol, 3.0 g (8.56 mmole) of 3,3-bis(p-diethylaminophenyl)acrolein and 1.1 g (9.80 mmole) of potassium t-butoxide were treated in the same manner as in Synthesis Example 13 to obtain 3.6 g (yield: 86%) of Illustrative Compound (38) (m.p. 135°–137° C.) as a crystal. The physical properties of the compound were as follows:

$^1$H-NMR (C$_6$D$_6$) δ ppm: 0.87, 0.88 (t, J=7.0 Hz, 12H), 2.98, 2.99 (q, J=7.0 Hz, 8H), 6.50–6.68 (m, 7H), 6.75–6.90 (m, 3H), 7.37–7.57 (AA'XX' system, 4H), MS (m/e value): 486 (M+), 471, 442, 427, 243

SYNTHESIS EXAMPLE 16

Synthesis of Illustrative Compound (48)

1.5 g (5.70 mmole) of 2-(O,O-dimethylphosphonyl)-1,3-benzodithiol, 2.0 g (4.69 mmole) of 3,3-bis(p-diethylaminophenyl)-2-phenylacrolein and 900 mg (8.02 mmole) of potassium t-butoxide were treated in the same manner as in Synthesis Example 13 to obtain 2.2 g (yield: 83%) of Illustrative Compound (48). The physical properties of the compound were as follows:

$^1$H-NMR (C$_6$D$_6$) δ ppm: 0.78, 0.90 (t, J=7.0 Hz, 12H), 2.82, 2.96 (q, J=7.0 Hz, 8H), 6.30 (d, J=8.9 Hz, 2H), 6.35–6.60 (m, 5H), 6.66 (d, J=7.7 Hz, 1H), 6.80 (s, 1H), 6.97–7.25 (m, 5H), 7.50 (t, J=8.8 Hz, 4H)

MS (m/e value): 562, 521 (M+), 560, 533, 502, 421, 362, 308, 280, 175, 148

SYNTHESIS EXAMPLE 17

Synthesis of Illustrative Compound (49)

1.1 g (4.20 mmole) of 2-(O,O-dimethylphosphonyl)-1,3-benzodithiol, 2.1 g (3.80 mmole) of 3-(p-dibenzylaminophenyl)-3-(p-diethylaminophenyl)-2-phenylacrolein and 500 mg (4.50 mmole) of potassium t-butoxide were treated in the same manner as in Synthesis Example 13 to obtain 2.5 g (yield: 96%) of Illustrative Compound (49). The physical properties of the compound were as follows:

$^1$H-NMR (C$_6$D$_6$) δ ppm: 0.79, 0.90 (t, J=7.0 Hz, 6H), 2.80, 2.95 (q, J=7.0 Hz, 4H), 4.18, 4.30 (s, 4H), 6.25 (d, J=8.9 Hz, 1H), 6.34–6.58 (m, 5H), 6.60–6.70 (m, 1H), 6.80 (d, J=16.5 Hz, 2H), 6.90–7.30 (m, 7H), 7.40–7.57 (m, 4H)

MS (m/e value): 686 (M+), 684, 683, 656, 594, 521, 438, 342, 152, 91, 65, 18

SYNTHESIS EXAMPLE 18

Synthesis of Illustrative Compound (50)

1.5 g (5.70 mmole) of 2-(O,O-dimethylphosphonyl)-1,3-benzodithiol, 2.0 g (5.40 mmole) of 2,3,3-tris(p-methoxyphenyl)acrolein and 900 mg (8.02 mmole) of potassium t-butoxide were treated in the same manner as in Synthesis Example 13 to obtain 2.0 g (yield: 73%) of Illustrative Compound (50) (m.p. 177°–178° C.) as a crystal. The physical properties of the compound were as follows:

$^1$H-NMR (C$_6$D$_6$) δ ppm: 3.18 (s, 3H), 3.25 (s, 3H), 3.30 (s, 3H), 6.40–6.57 (m, 3H), 6.58 (d, J=6.8 Hz, 2H), 6.65–6.70 (m, 2H), 6.72–6.83 (m, 4H), 7.08 (d, J=6.8 Hz, 2H), 7.32 (d, J=6.7 Hz, 2H), 7.40 (d, J=6.7 Hz, 2H)

MS (m/e value): 510 (M+), 370, 153, 78, 28

EXAMPLES 1 TO 9 AND COMPARATIVE EXAMPLE 1

(A) 0.2 g of Chlorodiane Blue was mixed with 4 g of a dichloroethane solution containing 5% of a polycarbonate resin (Jupilon E-2000, available from Mitsubishi Gas Chemical Company, Inc.). 20 ml of dichloroethane was added thereto. The mixture was pulverized to a size of 1 μm or less by means of a vibration mill to prepare a dispersion of a charge generating pigment. The dispersion was coated on an aluminum-deposited polyester film by means of a wire bar and dried at a temperature of 45° C. to form a charge generating layer having a thickness of about 1 μm thereon.

On the other hand, Illustrative Compounds (1), (6), (7), (15), (16), (35), (48), (49) and (50) previously set forth as typical examples of the compound represented by formula (I) were each dissolved in 2 g of a dichloroethane solution containing 10% of the above-mentioned polycarbonate resin in an amount of 0.2 g, respectively, to prepare charge transporting layer coating solutions. These coating solutions were each coated on the charge generating layer by means of a doctor blade to a dry thickness of about 20 μm and dried at a temperature of 80° C. for 2 hours to prepare photoreceptors.

(B) These photoreceptors were measured for electrophotographic properties in a static process by means of an electropaper analyzer (Type SP-428, available from Kawaguchi Denki Seisakusho). Specifically, these photoreceptors were subjected to corona discharge at −6 kV for 5 seconds so that they were charged. The resulting photoreceptors were measured for surface potential $V_O$ (minus volt). These photoreceptors were placed in a dark place for 5 seconds, irradiated with a light with an illuminance of 5 lux emitted from a tungsten lamp, measured for exposures $E_{\frac{1}{2}}$ (lux.sec) and $E_{1/16}$ (lux.sec) required to decay the surface potential to $\frac{1}{2}$ and 1/6, respectively, and then measured for residual potential $V_R$ (minus volt) developed after irradiation with a light at 5 lux for 10 seconds.

A photoreceptor was prepared in the same manner as in (A) except that as a comparative compound there was used the following compound which is not specifically described but falls within the claimed scope in JP-A-1-1401462 (m.p. 152°-153° C.) [Comparative Compound (1)]. The photoreceptor was then examined in the same manner as in (B). The results are set forth in Table 1.

Comparative Compound (1):

TABLE 1

| Example No. | Charge transporting substance | $V_0$ (−V) | $V_R$ (−V) | $E_{1/2}$ (l·s) | $E_{1/6}$ (l·s) |
|---|---|---|---|---|---|
| Example 1 | Illustrative Compound (1) | 824 | 0 | 3.9 | 9.1 |
| Example 2 | Illustrative Compound (6) | 906 | 15 | 5.4 | 12.3 |
| Example 3 | Illustrative Compound (7) | 1,046 | 4 | 5.0 | 11.8 |
| Example 4 | Illustrative Compound (15) | 1,020 | 10 | 3.9 | 9.0 |
| Example 5 | Illustrative Compound (16) | 910 | 20 | 3.9 | 10.1 |
| Example 6 | Illustrative Compound (35) | 926 | 10 | 4.7 | 17.7 |
| Example 7 | Illustrative Compound (48) | 800 | 0 | 2.8 | 7.5 |
| Example 8 | Illustrative Compound (49) | 840 | 2 | 4.0 | 12.0 |
| Example 9 | Illustrative Compound (50) | 940 | 0 | 2.8 | 7.5 |
| Comparative Example 1 | Comparative Compound (1) | 528 | 30 | 23.0 | Immeasurable |

Table 1 shows that all of the Illustrative Compounds of the present invention exhibit a high surface potential $V_O$ and a low residual potential $V_R$ as compared to Comparative Compound (1). Furthermore, these Illustrative Compounds of the present invention exhibit low $E_{\frac{1}{2}}$ and $E_{1/16}$ values required to decary the surface potential and thus provide a high sensitivity.

EXAMPLES 10 TO 20 AND COMPARATIVE EXAMPLE 2

Oxotitanium phthalocyanine was vacuum deposited on an aluminum-deposited polyester film under a reduced pressure of $10^{-6}$ Torr to a thickness of about 0.8 μm to form a charge generating layer thereon. Charge transporting layer coating solutions obtained by dissolving each of Illustrative Compounds (1), (6), (7), (11), (16), (19), (27), (35), (49) and (50) each in 2 g of a dichloroethane solution containing 10% of the same polycarbonate resin as used in (A) of Example 1 in an amount of 0.2 g were each coated on the charge generating layer by means of a doctor blade to a dry thickness of 22 μm and dried at a temperature of 80° C. for 3 hours to prepare photoreceptors. These photoreceptors were examined in the same manner as in (B) of Example 1.

A photoreceptor was then prepared in the same manner as described above except that as a comparative compound there was used Comparative Compound (1) as used in Comparative Example 1. The photoreceptor was examined in the same manner as in (B) of Example 1. The results are set forth in Table 2.

TABLE 2

| Example No. | Charge transporting substance | $V_0$ (−V) | $V_R$ (−V) | $E_{1/2}$ (l·s) | $E_{1/6}$ (l·s) |
|---|---|---|---|---|---|
| Example 10 | Illustrative Compound (1) | 962 | 0 | 2.1 | 5.6 |
| Example 11 | Illustrative Compound (6) | 1,004 | 2 | 1.8 | 3.4 |
| Example 12 | Illustrative Compound (7) | 1,158 | 14 | 1.0 | 2.0 |
| Example 13 | Illustrative Compound (11) | 1,380 | 10 | 1.6 | 3.9 |
| Example 14 | Illustrative Compound (16) | 900 | 4 | 1.1 | 2.5 |
| Example 15 | Illustrative Compound (19) | 1,014 | 8 | 1.5 | 3.5 |
| Example 16 | Illustrative Compound (27) | 680 | 0 | 1.0 | 1.8 |
| Example 17 | Illustrative Compound (35) | 874 | 0 | 1.1 | 2.0 |
| Example 18 | Illustrative Compound (48) | 680 | 2 | 1.8 | 3.8 |
| Example 19 | Illustrative Compound (49) | 720 | 2 | 2.0 | 4.2 |
| Example 20 | Illustrative Compound (50) | 680 | 0 | 2.4 | 5.8 |

TABLE 2-continued

| Example No. | Charge transporting substance | $V_0$ (-V) | $V_R$ (-V) | $E_{1/2}$ (l·s) | $E_{1/6}$ (l·s) |
| --- | --- | --- | --- | --- | --- |
| Comparative Example 2 | Comparative Compound (1) | 246 | 20 | 3.5 | 7.2 |

Table 2 shows that all of the Illustrative Compounds of the present invention exhibit a high surface potential $V_O$ and a practicably low residual potential $V_R$ as compared to Comparative Compound (1). Furthermore, these Illustrative Compounds of the present invention exhibit low $E_{\frac{1}{2}}$ and $E_{1/16}$ values required to decay the surface potential and thus provide a high sensitivity.

EXAMPLE 21

The photoreceptor obtained in Example 11 was further irradiated with a light of 10,000 lux.sec for 3 seconds to remove residual charges therefrom. The photoreceptor was then subjected to corona discharge at −6 kV for 5 seconds so that it was charged. The resulting photoreceptor was measured for surface potential $V_O$. The photoreceptor was then placed in a dark place for 5 seconds, irradiated with a light with illuminance of 5 lux emitted from a tungsten lamp, and then measured for half decay exposure $E_{\frac{1}{2}}$ and residual potential $V_R$. This cycle was repeated. The results are plotted in FIGS. 4 and 5.

Figure 4:
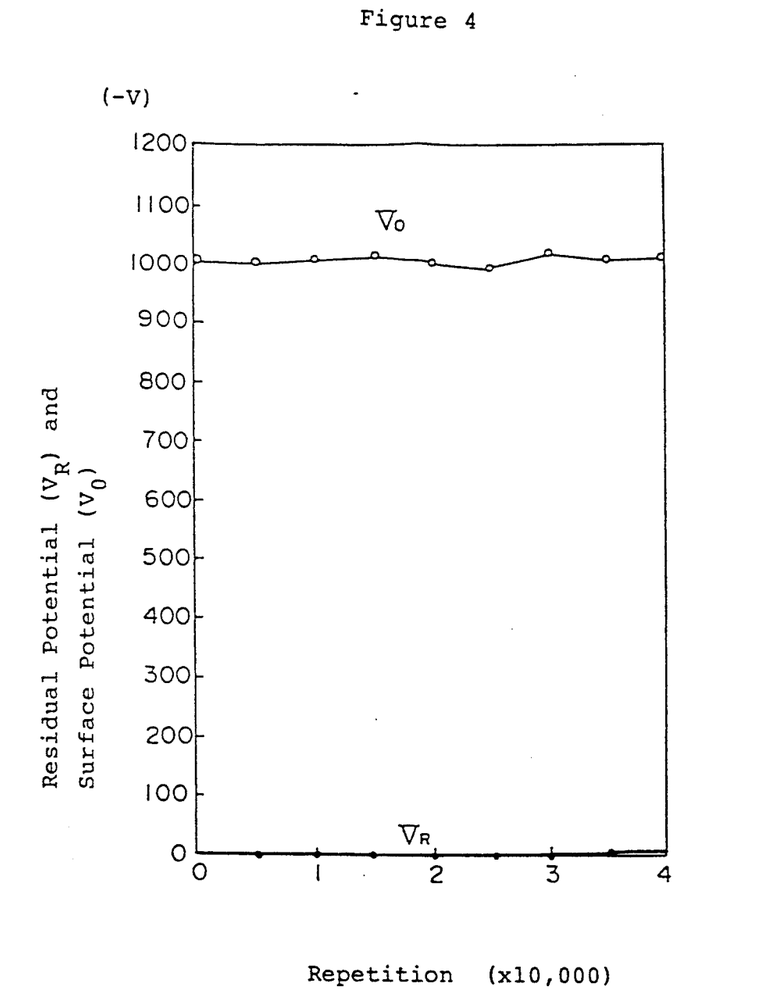
FIGS. 4 and 5 show each a graph illustrating the results of durability test on the electrophotographic photoreceptor of the present invention.
Figure 5:
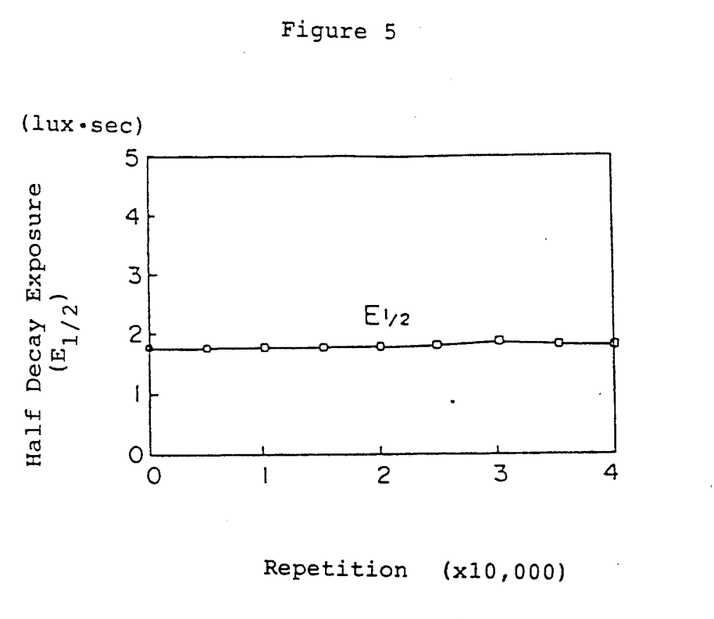

FIGS. 4 and 5 show that the present electrophotographic photoreceptor prepared in Example 11 exhibits little change in surface potential $V_O$, residual potential $V_R$ and half decay exposure $E_{\frac{1}{2}}$ even after repetition over 40,000 times.

As described above, the electrophotographic photoreceptor of the present invention exhibits properties useful for light-sensitive material. In particular, the electrophotographic photoreceptor of the present invention exhibits a high sensitivity and a low residual potential. The electrophotographic photoreceptor of the present invention is little subject to light fatigue even after repeated use, showing an excellent durability. Thus, the electrophotographic photoreceptor of the present invention exhibits properties which are most required in the field of electrophotographic process and is industrially advantageous.

While the invention has been described in detail and with reference to specific embodiments thereof, it will be apparent to one skilled in the art that various changes and modifications can be made therein without departing from the spirit and scope thereof.

What is claimed is:

1. An electrophotographic photoreceptor comprising an electroconductive support having a light-sensitive layer containing a charge generating substance and a charge transporting substance, wherein said charge transporting substance is a 1,4-benzodithiafulvene derivative represented by formula (I):

wherein $R^1$ represents a lower alkyl group, a benzyl group, a naphthyl group, or a phenyl group which may contain a substituent; $R^2$ represents a phenyl group which may contain a substituent or an N-alkyl-substituted carbazole group; $R^3$ represents a hydrogen atom or a phenyl group which may contain a substituent; $R^4$ represents a hydrogen atom, a lower alkyl group, a hydroxyl group, or an alkoxy group or an aryloxy group represented by $OR^5$; $R^5$ represents a lower alkyl group, a benzyl group, or a phenyl group which may contain a substituent; and n represents an integer of 0 or 1.

2. An electrophotographic photoreceptor as in claim 1, wherein n represents 0.

3. An electrophotographic photoreceptor as in claim 1, wherein n represents 1.

* * * * *